United States Patent [19]

Fertig, Sr. et al.

[11] Patent Number: 4,902,896
[45] Date of Patent: Feb. 20, 1990

[54] INFRARED FLUID ANALYZER

[75] Inventors: Glenn H. Fertig, Sr., Natrona Heights; Adrian C. Billetdeaux, Allison Park, both of Pa.

[73] Assignee: Mine Safety Appliances Company, Pittsburgh, Pa.

[21] Appl. No.: 47,650

[22] Filed: May 8, 1987

[51] Int. Cl.$^4$ .............................................. G01N 21/61
[52] U.S. Cl. ..................................... 250/343; 250/339
[58] Field of Search ................ 250/343, 344, 345, 339

[56] References Cited

U.S. PATENT DOCUMENTS

| 3,180,984 | 4/1965 | Fertig et al. | 250/343 |
| 3,562,522 | 2/1971 | Cederstrand et al. | 250/343 |
| 3,593,023 | 7/1971 | Dodson et al. | 250/343 |
| 3,869,613 | 3/1975 | Link et al. | 250/343 |
| 3,958,122 | 5/1976 | Jowett et al. | 250/345 |
| 4,200,791 | 4/1980 | Burough | 250/343 |
| 4,205,913 | 6/1980 | Ehrfeld et al. | 250/343 |
| 4,274,091 | 6/1981 | Decker | 250/339 |
| 4,437,005 | 3/1984 | Ophoff et al. | 250/343 |
| 4,692,621 | 9/1987 | Passaro et al. | 250/343 |

FOREIGN PATENT DOCUMENTS

| 1570899 | 7/1980 | United Kingdom . | |
| 8300613 | 3/1983 | World Int. Prop. O. | 250/343 |

Primary Examiner—Constantine Hannaher
Attorney, Agent, or Firm—Reed Smith Shaw & McClay

[57] ABSTRACT

An infrared fluid analyzer for the detection of end tidal $CO_2$. The analyzer is comprised of an IR source that irradiates a chamber filled with gas. $CO_2$ present in the chamber absorbs the IR radiation at a certain wavelength. An IR detector determines the amount of IR radiation passing through the chamber unabsorbed and produces a signal corresponding to the $CO_2$ in the chamber. At predetermined intervals a zero gas is reintroduced into the chamber for the system to be recalibrated. A span gas is only needed initially for calibration purposes.

8 Claims, 2 Drawing Sheets

INFRARED FLUID ANALYZER

FIELD OF THE INVENTION

The present invention relates to fluid detection. More specifically, the present invention relates to the detection of end-tidal $CO_2$ using infrared radiation but which does not require the constant presence of a span fluid for the purposes of recalibration.

BACKGROUND OF THE INVENTION

There is a great need for the accurate detection of end-tidal $CO_2$ with regard to the surgical environment. The production of end-tidal $CO_2$ is indicative of how well a patient is obtaining necessary oxygen from inhaled air. The end-tidal $CO_2$ is given off by the blood as it absorbs fresh oxygen in the lungs. If there is a decrease in the concentration of end-tidal $CO_2$ in the exhalation breath of a patient during surgery, then steps must be taken by the surgical team to counter the end-tidal $CO_2$ decrease. Commonly, a decrease in end-tidal $CO_2$ means that there is too much anesthesia fluid going to the patient, essentially smothering the patient.

Infrared fluid detectors are currently available to detect end-tidal $CO_2$. However, they lack the ability to be frequently and easily recalibrated to compensate for any instabilities in the respective detectors that may arise to yield a false reading. In addition, in the detectors where some type of calibration is preferred, the presence of a zero fluid and a span fluid are required. For instance, U.S. Pat. No. 4,205,913 to Ehrfeld, et al. describes a typical IR fluid detection apparatus which uses a filter heel disposed in the IR beam path to act as a chopper. The chopper causes a reference signal to pass as well as a signal proportional to the concentration of fluid being analyzed to pass. The IR radiation passing through a measuring cuvette is detected by an IR detector. A concentration value is subsequently computed.

U.S. Pat. No. 4,437,005 to Ophaff, et al. describes a nondispersive infrared fluid analyzer that utilizes thermal energy to expand the volume of a fluid. The expanded fluid whose increase corresponds to the concentration of reactive fluid in the volume, exerts a corresponding pressure on a diaphragm capacitor. The capacitor delivers an electrical measuring signal in proportion to the amount of movement on the diaphragm.

In U.S. Pat. No. 4,200,791 there is described a fluid analyzer using nondispersive infrared radiation. A rotary filter wheel positioned between an IR source and a fluid sample cell causes an IR detector to produce a pulsating output. The output is processed indicating the concentration of the constituents of the fluid mixture in the sample cell.

U.S. Pat. No. 3,180,984 to Fertig, et al. describes a stabilized comparison analyzer using radiation in the visible and infrared range. The radiant energy is produced from two sources of light energy and directed into a sample and comparison cell, wherein the radiation therefrom is converged onto a detector. A power oscillator circuit alternately energizes the sources to render the effect of alternately interrupting the beams. Initially, the amount of energy of each beam reaching the detector is equal. During analysis the measure of imbalance between the two beams is the signal produced from the detector and corresponds to the type of fluid being analyzed.

British Pat. No. 1,570,899 to Allred Chemical Corporation describes an infrared fluid analyzer. Therein infrared light is passed having a selective frequency range in the region of air absorption based for preselected molecular species. A secondary filter transmits light having a plurality of discrete frequencies which provides a detectable signal. The detectable material is transmitted through fluideous material whereby the intensity of the signal changes in proportion to the concentration of the preselected species.

SUMMARY OF THE INVENTION

Accordingly, one object of the present invention is to provide an infrared fluid analyzer that can be frequently and accurately recalibrated so the correct concentration of a subject fluid is determined.

Another object of the present invention is to provide an infrared fluid analyzer that does not require the presence of a span fluid for calibration purposes after an initial calibration.

Another object of the present invention is to provide a signal to a microprocessor corresponding to the percent absorption of infrared radiation passing through a subject fluid, as well as the pressure and temperature of the subject fluid, so the microprocessor determines a correction factor to apply to the percent absorption signal to compensate for any error in the signal.

Another object of the present invention is to provide an infrared detector that provides an accurate concentration of end-tidal $CO_2$ exhaled by a person in a surgical environment.

These and other objects of the present invention are accomplished with an infrared fluid analyzer comprising means for producing infrared radiation; a chamber transparent to infrared radiation housing the fluid to be analyzed, said chamber disposed to receive the radiation produced by the source means; means for detecting the radiation produced by the source means which passes through the chamber, said detecting means producing a signal corresponding to the amount of radiation detected; means for providing a first fluid to the chamber to be analyzed, and at least a second zero fluid, frequently, in order to recalibrate the detector; means for correcting the signal produced by the detecting means to compensate for instabilities therein, said correcting means controlling the fluid providing means to determine which fluid is to be provided to the chamber; and means for displaying the corrected signal to show the concentration of fluid reactive to the IR radiation in the chamber.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
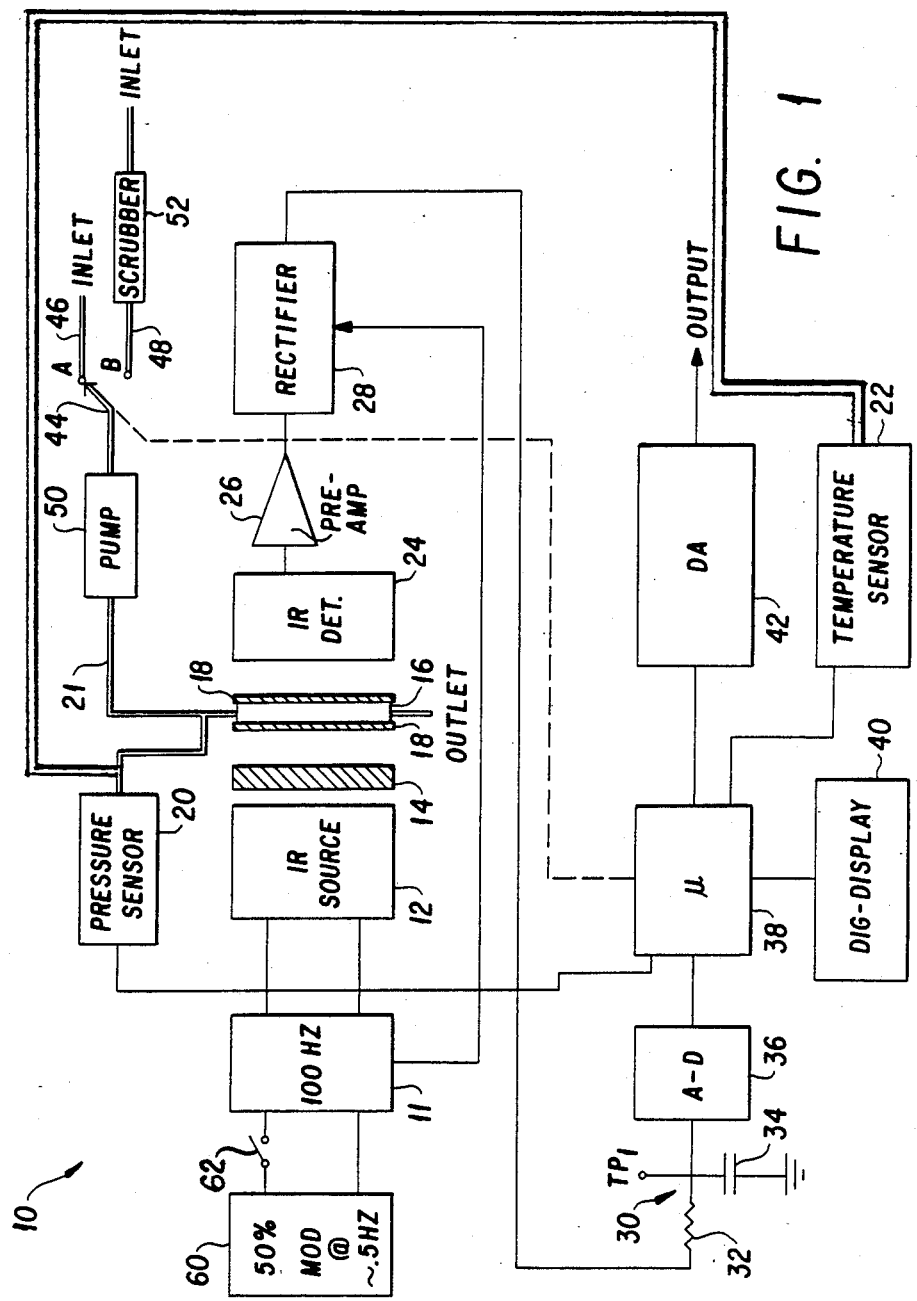
FIG. 1 is a schematic diagram of the infrared fluid analyzer.

Referring now to the drawings, wherein like reference numerals designate identical or corresponding parts throughout, and more particularly to FIG. 1 thereof, numeral 10 designates an infrared fluid analyzer. The fluid analyzer 10 is comprised of an IR source 12 that is turned on and off by an oscillator 11. The IR source 12 provides IR radiation at a discrete wavelength to a chamber 16 housing a fluid some part of which may resonate at the IR radiation wavelength. The IR radiation that passes through the chamber 16 is received by an IR detector 24 that senses the amount of radiation incident upon it. The detector 24 produces a signal proportional to the IR radiation detected which is rectified by a rectifier 28. The rectified signal is passed to a microcomputer 38 where it is saved in memory. A conversion factor is applied to the saved signal after which it is displayed. The correction factor is determined by first measuring the amount of IR radiation passing through a noncontaminated or zero fluid which is unreactive to the IR radiation having a particular wavelength. Then the amount of IR radiation passing through a known concentration of a span fluid is measured. (The different fluids are obtained by the processor 38 controlling a solenoid 44 that governs which fluid supply 46,48 supplies the fluid to the chamber 16 to be analyzed.) With the two measurements from the zero fluid and the span fluid, any concentration of reactive fluid in the chamber 16 can be analyzed. Additionally, the system can be frequently recalibrated by having only the zero fluid being reintroduced to the chamber and the detected value of passed radiation through the chamber becoming the reference point from which all calculations are based.

More specifically, an IR source 12 produces IR radiation according to an oscillator 11 which turns the source 12 on and off. The IR source could provide IR radiation having a discrete wavelength at which the fluid subject to detection resonates. The IR source 12 could also be a blackbody source, providing IR radiation across the entire spectrum. In the latter case, an IR filter 14, such as an IR dielectric type filter, could be used for limiting the spectral emission to a desired wavelength. If an IR filter 14 is used, it is placed between the IR source 12 and a chamber 16 through which the fluid subject to detection is flowing.

The chamber 16 must have IR transparent windows 18 through which IR radiation produced by IR source 12 passes. A fluid flowing through the chamber 16 is subjected to the IR radiation. IR radiation is absorbed by the fluid if the IR radiation is at the wavelength which at least a component of the fluid resonates. Then less IR radiation passes through the chamber. The actual amount of radiation passing through the chamber 16 depends on the amount of the fluid which resonates in the chamber. (For a more complete discussion of IR radiation analysis see "Instrumental Methods of Analysis" by Willard, Third Edition, D. Van Nostrad, January, 1958, pages 139-154). Factors such as pressure, temperature and the volume of the fluid in the chamber 16 affect the amount of fluid in the chamber and consequently the radiation absorbed. These factors must be fixed if possible or at least compensated for if there is variation in them to attain a standard reading over time. The volume can be fixed by making the chamber 16 of a rigid material. The pressure and temperature are more difficult to fix. By placing a pressure sensor 20 and a temperature sensor 22 in a fluid supply channel 21 at a location just before fluid enters the chamber 16, the pressure and temperature of the fluid can be determined. The identified readings can be used to modify a signal corresponding to the amount of fluid subject to detection as discussed more fully below. For a given pressure and temperature, the amount of IR radiation absorbed is a function of the distance between the two windows 18 through which the IR radiation must pass. The greater the distance between windows 18, the more material present, and the more IR radiation absorbed. More importantly, what is actually measured by an IR detector 24, situated in line with the IR source 12 but with the chamber 16 therebetween is the actual radiation passing, that is, the incident radiation versus the absorbed radiation. The signal produced by the IR detector is proportional to the present absorption of the IR radiation as it passes through the chamber 16. This information is carried in the IR detector 24 signal, by way of the peak-to-peak value or amplitude of the signal. The IR detector signal 24 is an AC signal due to oscillator 11 turning the IR source 12 on and off. One possible detector that can be used is an OptoElectronics OTC-12-5/OTC-12-7 Series two stage thermoelectrically cooled lead selenide detector.

The AC IR detector signal is amplified by an AC pre-amplifier 26. The output of the AC pre-amplifier 26 is connected to a synchronous rectifier 28 which rectifies the pre-amplifier 26 output, and produces a pulsating DC signal. The rectifier 28 is also controlled by the oscillator 11. When the oscillator 11 is on and radiation is being produced by source 12, the rectifier 28 does not rectify the output of the pre-amplifier 26. Only when the oscillator 11 is not causing the IR source 12 to radiate does the rectifier 28 rectify the output of the preamplifier 26. The AC amplifier 26 and rectifier 28, along with the IR source turning on and off are used because a more accurate signal is created. If the IR source was maintained on constantly, other problems, such as cooling of the detector 24, have to be dealt with that add complexity to the design.

The pulsating DC signal produced by the rectifier 28 is fed into a low pass filter 30 comprised of a resistor 32 and a capacitor 34 as is well known in the art. The filter is used to reduce or eliminate any AC ripple in the DC signal at test point TP1. The low pass filter 30 also acts as an averager and the resulting DC signal corresponds to the average inputted signal to the filter over a predetermined period of time.

Figure 2:
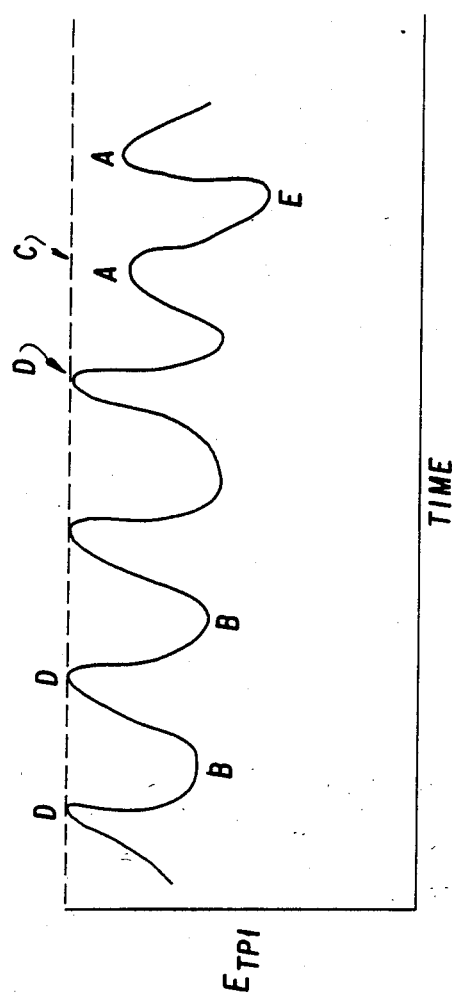
FIG. 2 is a graph showing the concentration of fluid in the detector reactive to the infrared radiation.

An analog to digital converter 36 monitors the DC signal at TP1 and converts the DC signal to a digital signal. The digital signal from the converter 36 is a digital word having a value proportional to the DC input signal. This digital word is received by a microprocessor 38. The microprocessor 38 also receives the output from the pressure sensor 20 containing information about the detected pressure of the fluid, and the output from the temperature sensor 22 containing information about the detected temperature of the fluid. The processor 38 takes the received signals from the pressure sensor 20, temperature sensor 22 and the converter 36 and calculates a corrected percent absorption factor. The correction factor for both the temperature and pressure is approximately a linear function. The corrected signal of the percent absorption is passed either to a digital display 40 for a digital read-out of the percent absorption or to a digital to analog convertor 42 for possible analog display. The processor, in addition also controls a sample fluid solenoid 44 that determines what fluid supply 46, 48 provides fluid to enter the chamber 16, be it for analysis or calibration purposes as is more fully discussed below. The signal present at TP1 is depicted in FIG. 2. As is explained more fully below, the graph shows the IR radiation signal as a function of time with respect to the fluid in the chamber 16. Point D depicts the situation when no fluid reactive to IR radiation is present in the chamber 16. Point B depicts the situation when the chamber 16 is entirely filled with reactive or span fluid. Points A and E represent concentrations of reactive fluid in the chamber 16 between the extremes of that measured at points B and D, for instance during inhalation nd exhalation, respectively. Point C represents where point D should be located, if instabilities are compensated for in the system that cause error in the signal. However, at the time points A and E are determined, the system is not calibrated properly, hence the reason why point E is lower than point B.

To better understand the purpose of the solenoid valve 44 and fluid supplies 46 and 48, an explanation of the production of the signal at TP1 follows. Besides the IR radiation that strikes the IR detector to cause a signal to be proportional thereto, instabilities inherent in the system also contribute to the ultimate signal produced. Instabilities found in analyzers are manifested as changes in IR signal strength, detector sensitivity, and electronic gain.

Other conditions causing instabilities are liquid or dirt on chamber windows 18.

The equation for the change in signal output at TP1 is shown in EQ1.

(EQ1): Change in signal at TP1=beam energy incident on the IR detector×% absorption×electronic gain It can be seen, any change in the beam energy or detector sensitivity can be corrected with a change in gain. A second and preferred method to compensate for any change would be a correction factor computed by the microprocessor. This correction factor could be determined by the computer frequently receiving information concerning the percent absorption of known concentrations of fluids as detected at any given moment to recalibrate the system. This is the purpose of solenoid 44 and the fluid supplies 46, 48.

In the operation of the invention the frequent recalibration of the system is carried out by the processor 38 first switching solenoid valve 44 to position B. In this position fluid having no reactivity with the IR radiation, otherwise known as zero fluid, is pulled by pump 50 through a chemical scrubber 52 to remove any contaminants and fluid reactive to the IR radiation. (One possible chemical scrubber is Ascarite II). The contaminant free fluid then flows into the chamber 16.

After the fluid is placed in the chamber 16, and, a signal is developed corresponding to the fluid therein, the microprocessor reads the output of the A to D converter 36 and stores the value in the processor memory. This value is depicted in FIG. 2, point D.

Next, the processor 38 switches the solenoid 44 to position A. In this position a span fluid with a known concentration is introduced into the chamber 16. The microprocessor 38 then reads the new value at TP1 via the A to D converter 36 and stores this span value in its memory. This value is depicted in FIG. 2 point B.

At this time, the microprocessor 38 has enough information to evaluate any signal at TP1 and output a signal proportional to any fluid concentration which might be in the cell. The signal out is depicted in FIG. 2 as points A and E. During use in surgery fluid supply A is a tube placed in the mouth of a patient. When supply A is chosen the pump draws in whatever fluid is present in the patient's mouth. Upon inhalation, only air is drawn in. Upon exhalation, the breath produced from the lungs is drawn in.

As pointed out previously, the instrument sensitivity can only change if there is a system gain change or equivalent. Referring to FIG. 2, the effective gain change can be corrected by putting, for instance in the surgical setting, $CO_2$ free fluid in the chamber 16 and the gain adjusted to bring the output at TP1 back to point C in FIG. 2. By frequently reintroducing $CO_2$ free fluid into the chamber 16, the instabilities in the system can be compensated for and an accurate reading of the percent absorption of IR radiation for a desired fluid be determined. Also, it should be emphasized, by following the above described technique, after the span fluid is introduced at the beginning thereof and point B determined, there is no further need for the use of the span fluid. This is because any change in the signal can be determined relative to point D by comparing subsequent readings of zero fluid thereto and recalibrating. Point D, that identified with only zero fluid present is fixed relative to point B. When the zero fluid and the span fluid are first introduced into the chamber 18 for calibration, and at subsequent times when zero fluid is reintroduced to the chamber 16 to recalibrate the system, a modulator 60 is activated by switch 62 being closed. Modulator 60 provides 50 percent modulation to the oscillator 11 at a frequency of about 0.5 HZ. The purpose of modulator 60 is to mimic the breathing of a person and simulate the breathing pattern thereof so the system can be accurately calibrated for actual human breathing.

Lastly, it should be mentioned that there are a variety of designs that can be implemented to carry out the invention. For instance, instead of an AC signal being produced by the detector corresponding to the amount of end tidal $CO_2$ in the chamber, a DC signal can be produced which would allow for the deletion of the rectifier. Also, a black body source without a filter allowing only a desired wavelength to pass can be used with either a broad body detector or a selective detector. In the former case, there would still be a determination of the variation of the signal. This would provide information with regard to the difference of end tidal $CO_2$. The difference in the operation which would have to realized is that other components of the exhaled breath could react with the infrared radiation. For instance, water in breath also reacts with IR energy, but water is of a much smaller percentage of the total breath, about 3%, than $CO_2$, which is about 10%. So a relatively accurate result can still be obtained. Similarly, for the latter situation, if a broad spectrum of IR radiation is used with a selective detector to the wavelength that reacts with $CO_2$, again the difference in the signal during breathing can be developed with a fairly accurate result.

Obviously, numerous (additional) modifications and variations of the present invention are possible in light of the above teachings. It is therefore to be understood that within the scope of the appended claims, the invention may be practiced otherwise than as specifically described herein.

What is claimed is:

1. An infrared fluid analyzer comprising:
    means for producing infrared radiation at a constant predetermined wavelength;
    a chamber transparent to infrared radiation housing the fluid to be analyzed, said chamber disposed to receive the radiation produced by the radiation producing means;

means for detecting the radiation produced by the radiation producing means which passes through the chamber, said detecting means producing a signal corresponding to the amount of radiation detected;

means for providing a first fluid to the chamber to be analyzed, and at least a second zero fluid in order to determine instabilities therein;

means for correcting the signal produced by the detecting means when the first fluid is in the chamber to compensate for instabilities therein measured when the second zero fluid is in the chamber, said correcting means controlling the fluid providing means to determine which fluid is to be provided to the chamber; and means for displaying the corrected signal to show the concentration of fluid reactive to the IR radiation passing through the chamber.

2. An analyzer as described in claim 1 wherein the means for producing infrared radiation includes a blackbody IR source with an IR filter allowing only IR radiation with a desired wavelength to pass, said filter positioned between the IR source and the chamber, and an oscillator to turn on and off the IR source.

3. An analyzer as described in claim 2 wherein the radiation detecting means includes an IR detector positioned to receive IR radiation passing through the chamber, said detector producing a signal corresponding to the detected radiation; an amplifier to amplify the signal produced by the detector; a rectifier that receives and rectifies the amplified signal, said rectifier connected to and controlled by the oscillator so the amplified signal is rectified only when the IR source is off; and a low pass filter which receives the rectified signal and averages it over time to produce a steady DC signal that corresponds to the IR radiation detected by the detector.

4. An analyzer as described in claim 3 wherein the means for correcting the signal produced by the low pass filter of the detecting means includes an A/D convertor which converts the signal from the low pass filter to a digital signal; a microprocessor, which receives the digital signal and controls the fluid providing means; and a pressure sensor and a temperature sensor, each located in the fluid providing means at a location just before the fluid enters the chamber, and each providing a signal to the processor corresponding to the pressure and temperature, respectively, sensed, said processor computing a correction factor from the pressure and sensor signal provided thereto to apply to the signal provided by the A/D convertor to more accurately determine the concentration of fluid reactive to IR radiation passing through the chamber.

5. An analyzer as described in claim 4 wherein the fluid providing means is comprised of a solenoid controlled by the processor that determines whether a first fluid supply and at least a second zero fluid supply, each connected to solenoid, suppliers fluid to the chamber via a supply channel, said pressure and temperature sensors located in the supply channel.

6. An analyzer as described in claim 5 wherein the display means includes a digital display connected to the processor and a digital to analog convertor separately connected to the processor, said digital to analog convertor connected to an analog display.

7. An infrared fluid analyzer comprising:

means for producing periodic IR radiation at a constant predetermined wavelength at which the fluid resonates;

a chamber housing the fluid, the chamber being transparent to IR radiation and disposed to receive the IR radiation produced from the IR radiation means;

IR detector means disposed to receive IR radiation passing through the chamber, said IR detector producing an electric signal corresponding to the amount of IR radiation detected;

a fluid supply channel connected to the chamber through which fluid is introduced into the chamber;

a pressure sensor disposed in the fluid supply channel to detect the pressure of the fluid before it enters the chamber, the pressure sensor producing a signal corresponding to the pressure detected;

a temperature sensor disposed in the fluid supply channel to detect the temperature of the fluid before it enters the chamber, said temperature sensor producing a signal corresponding to the temperature sensed;

a computer which receives the IR detector means signal, the pressure sensor signal and the temperature sensor signal and calculates the accurate amount of fluid present in the chamber;

a first fluid source connected to the fluid supply channel, said first fluid being reactive with the IR radiation produced by the IR radiation source;

a second fluid source connected to the fluid supply channel, said second fluid being unreactive with the IR radiation produced by the IR radiation source; and valve means for controlling whether the first or second fluid supply supplies the chamber said valve having at least two inlet ports to receive at least the first fluid or the second fluid, said valve activated by the computer, so when said second fluid enters the chamber, the computer measures the IR detector means signal and recalibrates the base line from which the amount of the first fluid present in the chamber is determined.

8. An apparatus as described in claims 6 or 7 wherein the first fluid is end-tidal $CO_2$.

* * * * *